United States Patent [19]

Holloway

[11] 4,381,780
[45] May 3, 1983

[54] SUSTAINED RELEASE DELIVERY SYSTEM

[75] Inventor: Joseph W. Holloway, Maryville, Tenn.

[73] Assignee: Research Corporation, New York, N.Y.

[21] Appl. No.: 226,391

[22] Filed: Jan. 19, 1981

[51] Int. Cl.³ .......................... A61M 7/00; A61D 7/00
[52] U.S. Cl. ........................................ 604/892; 424/21
[58] Field of Search .............................. 128/222–223, 128/260; 424/19, 21, 27

[56] References Cited

U.S. PATENT DOCUMENTS

| | | | |
|---|---|---|---|
| 4,034,756 | 7/1977 | Higuchi et al. | 128/130 |
| 4,165,998 | 8/1979 | Adams et al. | 424/21 |
| 4,217,898 | 8/1980 | Theeuwes | 128/260 |
| 4,249,531 | 2/1981 | Heller et al. | 128/260 |
| 4,290,426 | 9/1981 | Luschen et al. | 128/260 |
| 4,308,250 | 12/1981 | Griffin et al. | 128/260 |

Primary Examiner—C. Fred Rosenbaum
Attorney, Agent, or Firm—Scully, Scott, Murphy & Presser

[57] ABSTRACT

A device and a method for the prolonged administration of controlled amounts of a substance are disclosed. In one embodiment, the device is disclosed for the prolonged administration of dosages of a therapeutic, additive, or nutrient substance into the reticulorumen of a ruminant, comprising a body having an interior chamber, at least one end of said chamber open to the exterior of said body, said body made from a material which maintains its integrity in the reticulorumen environment, a plurality of degradable, such as cellulosic, partitions within said interior chamber connected to or fitting closely against the inner walls of said body, said partitions dividing said interior chamber into a series of compartments, each compartment containing a dosage of the therapeutic, additive or nutrient substance, said partitions arranged in an order to be degraded sequentially upon exposure to the reticulorumen environment thereby releasing sequentially the dosages of the substance into the reticulorumen, and retaining means provided by said body to retain the device within the reticulorumen of the ruminant.

39 Claims, 3 Drawing Figures

SUSTAINED RELEASE DELIVERY SYSTEM

BACKGROUND OF THE INVENTION

This invention relates to a device and a method for the sustained release of a substance. In one embodiment, this invention relates to a bolus which is administered orally to a ruminant and which dispenses controlled amounts of a therapeutic, additive or nutrient substance over a prolonged period of time into the reticulorumen of the ruminant.

It is well known that ruminant animals, such as beef cattle and sheep, are able to digest large quantities of low quality feeds. These feeds, comprising mostly cellulose are swallowed with little chewing. They are ingested into the largest of four stomachs, called the rumen. The rumen is not a true stomach inasmuch as it contains no digestive glands. It is more in the nature of a storage compartment, a mixing organ, and a reservoir containing a large concentration of bacteria. The bacteria in the rumen break up the complex cellulose components of the feed into simpler substances which are more readily digested. The feed is then regurgitated by the animal, masticated into finer particles, and reswallowed. When the particles are reduced to a certain critical size, they pass out of the rumen for further digestion in the true stomach.

The cattle industry has long sought devices which release therapeutic, additive or nutrient substances into the rumen in a controlled fashion over an extended period of time. The recent development of high quality feed additives, such as the feed additive Rumensin ® (a trademark of Eli Lilly and Company), has increased the need for such devices. These feed additives improve feed efficiency and promote growth of the cattle. However, the additives must be given orally and must be consumed in small quantities at frequent and regular intervals. These requirements make it difficult to administer the feed additives properly.

Most beef cows and growing calves are allowed to graze over a wide area of pasture land. Thus, it is highly inconvenient for cattle ranchers to administer a dosage of the feed additives daily. Furthermore, many cattle ranchers are also farmers and are unable to devote the time necessary to administer the feed additives. No system or device has yet been disclosed by which these feed additives can be satisfactorily and inexpensively dispensed in the manner required to grazing ruminants.

Several sustained release delivery systems are disclosed in the prior art. U.S. Pat. No. 3,056,724 (Marston) discloses therapeutic pellets for ruminants. These pellets rely upon their size and density to remain inside the rumen, and upon their chemical composition for gradual dissipation of the active agent. U.S. Pat. No. 3,844,285 (Laby) discloses an expandible device for administration to ruminants. The device has a body portion comprising or containing an effective amount of an active agent. Sustained release is achieved by incorporating or coating the active agent with materials having low solubility or permeability in rumen liquor. The device, in a compressed configuration, is given orally to the ruminant. After entering the rumen, the device assumes an expanded configuration and is thereby retained within the rumen.

Other patents, such as U.S. Pat. Nos. 3,608,549 (Merrill), 4,135,514 (Zaffaroni et al.), 4,180,558 (Goldberg et al.), and 4,207,890 (Mamajek et al.), disclose devices for the sustained release of drugs to warm blooded animals, especially humans. These devices depend upon an unpredictable rate of release. None of the devices described in these patents is particularly suitable for the prolonged administration of feed additives in the quantity required to ruminants in a predictable controlled manner.

Thus, there remains a need for a simple and inexpensive device to release a substance in measured amounts over a prolonged period of time.

There is also a need for a device of this kind which is particularly suitable for the administration of therapeutic, additive or nutrient substances into the reticulorumen of ruminants.

There is also a need for a device of this kind which meets the needs of the cattle industry.

SUMMARY OF THE INVENTION

These and other objects are accomplished by means of the present invention which, broadly, comprises a device for the prolonged administration of a substance, comprising:
  a body having an interior chamber, at least one end of said chamber in fluid communication with the exterior of said body,
  said body made from a material which maintains its integrity during the administering period; and
  a plurality of partitions positioned within said interior chamber and connected to or closely fitting against the inner walls of said body,
  said partitions made from a material which degrades during the administering period upon fluid exposure to the exterior of said body,
  said partitions dividing said interior chamber into a sequence of compartments, each compartment containing a dosage of the substance to be administered,
  said partitions arranged in an order to be degraded sequentially, thereby releasing sequentially the dosages of the substance.

By "maintains its integrity", it is meant that the body is not degraded when the device is in its environment of use.

When a device such as this is in its environment of use, i.e., during the administering period, the dosages of the substance are retained in their compartments by the partitions. The partitions do not permit release of the substance as long as they remain intact. It is only upon exposure of the partitions to the environment of use in sequential order that the partitions are degraded sequentially and release the dosages of the substance over an extended period of time.

More narrowly, the present invention comprises a device for the prolonged administration of dosages of a therapeutic, additive or nutrient substance into the reticulorumen of a ruminant, comprising:
  a body having an interior chamber, at least one end of said chamber open to the exterior of said body,
  said body made from a material which maintains its integrity in the reticulorumen environment,
  a plurality of degradable, such as cellulosic, partitions within said interior chamber and connected to or closely fitted against the inner walls of said body,
  said partitions dividing said interior chamber into a sequence of compartments, each compartment containing a dosage of the therapeutic, additive or nutrient substance, said partitions arranged in an order to be degraded sequentially upon exposure to the reticulorumen environment, thereby releasing sequentially the dosages of the substances into the reticulorumen; and retaining means provided by said body to retain the device within the reticulorumen of the ruminant.

In this embodiment, the device of the present invention may be used to deliver daily doses of Rumensin ® or other feed additives to cattle, sheep or other ruminants over a prolonged period of time. In addition, other ingredients can be also administered to ruminants with the device of the present invention.

DETAILED DESCRIPTION OF THE INVENTION

Figure 1:
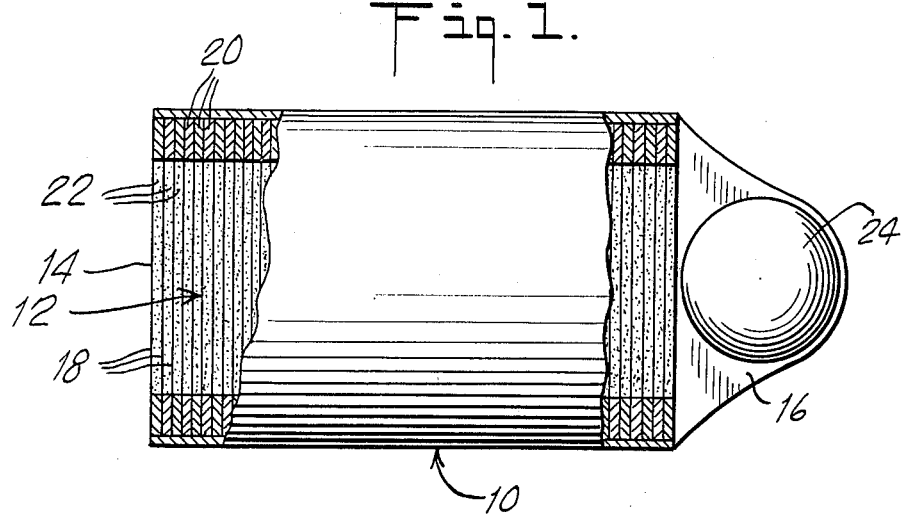
FIG. 1 is a view of a device according to the present invention adapted for the sustained release of therapeutic, additive or nutrient substances into the reticulorumen of a ruminant.
Figure 2:
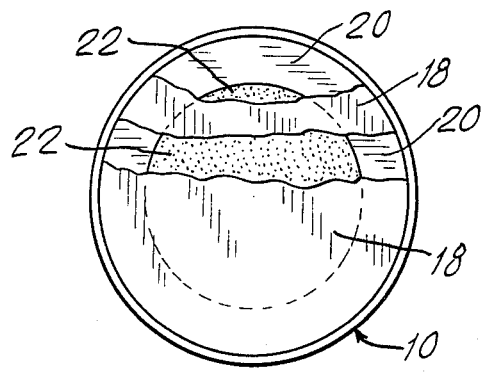
FIG. 2 is a broken away sectional view of the device of FIG. 1 from its open end.

Referring to FIGS. 1 and 2, a bolus is shown which contains therapeutic, additive or nutrient substances for delivery into the reticulorumen of a ruminant over a prolonged period of time. The bolus comprises a substantially cylindrical body or shell 10 having a hollow interior chamber 12, an open end 14, and a closed end 16. The body 10 is made from a material or is coated with a material which is resistant to biochemical activity inside the reticulorumen. For example, body 10 may be made from a resistant epoxy, polyethylene, or polypropylene. Alternatively, body 10 may be made from wood or metal and coated with a resistant epoxy, polyethylene, or polypropylene.

Inside the bolus, partitions 18 separated from each other by spacers 20 divide interior chamber 12 into a sequence of compartments 22. Each compartment 22 contains a dosage of the therapeutic, additive or nutrient substance to be released into the reticulorumen of the ruminant.

Spacers 20 are attached to or fit closely against the inner wall of body 10. Spacers 20 comprise rings made from paper or some other cellulosic material which dissolves in the reticulorumen environment.

Partitions 18 comprise solid discs of substantially the same diameter as interior chamber 12. Partitions 18 are held in place by spacers 20. Alternatively, spacers 20 may be omitted. Partitions 18 will then be held in place by their close fit against the inner wall of body 10 and by the substance placed inside compartments 22.

Partitions 18 are made from a material which is degraded upon exposure to the reticulorumen environment. For example, the partitions may be made from paper. The partitions retain the dosages in their compartment until they are exposed to the reticulorumen environment. The specific material selected determines the frequency of delivery of dosages. Table I illustrates the relative degradability of partitions made of various materials in the reticulorumen of beef cattle.

TABLE I

| Partition | Days/Partition Degraded |
|---|---|
| Wax Paper | 5.4 |
| Resin Treated Paper | 1.5 |
| 40 lb. Basis Kraft Paper | 1.3 |
| 75 lb. Basis Kraft Paper | 1.0 |
| Paraffin | 0.4 |

Table I demonstrates that dosages of the therapeutic, additive or nutrient substance will be delivered daily into the reticulorumen of beef cattle if the partitions are made from a kraft paper of 75 lb. basis.

Retaining means are needed to retain the bolus within the ruminant. For example, weight means which impart to the bolus a specific gravity of at least about 1.5, preferably about 1.5-7.0, can serve as the retaining means. In the embodiment shown in FIG. 1, a steel ball 24 serves as the weight means. The steel ball 24 is attached to the closed end 16 of body 10. For example, the steel ball 24 may be enclosed within an epoxy shell as illustrated.

The bolus should be small enough to pass readily into the reticulorumen of the particular ruminant. The bolus of FIG. 1 should be no larger than 25 mm diameter and 100 mm long for administration to a calf weighing 180 kg. A bolus of this size would readily pass into the calf's reticulorumen.

The dimensions of each of the compartments 22 may also be varied to contain the desired dosage of the substance to be released. Compartments that are 1 mm deep and 18 mm in diameter, as viewed in FIG. 1, are adequate to deliver a daily dose of 300 mg Rumensin ® to a calf weighing 180 kg. Thus, the bolus of FIG. 1 may be used to deliver approximately 90 daily doses of Rumensin ® to growing calves.

In use, the bolus is administered orally to the ruminant, for example, by means of a common balling gun apparatus. The bolus passes through the esophagus into the reticulorumen of the ruminant. Due to its high specific gravity, it settles into the dorsal reticulorumen and is retained there. The body or shell 10 protects the partitions from bacterial attack except from the direction of open end 14. The first partition is degraded or eroded by the bacteria, opening the first compartment and releasing a dose of the therapeutic, additive or nutrient substance contained therein. Upon opening of the first compartment, the second partition becomes exposed to bacterial attack from the reticulorumen environment. The process repeats itself until all doses have been released at regular intervals. The material selected for the partitions determines the frequency of dosage release.

When all the doses have been released, the bolus remains as a hollow shell inside the animal. The bolus can be allowed to remain there without causing any problems. If desired, each twentieth spacer can be made of a relatively digestible wood, such as oak wood, and may be left free from the epoxy coating. The shell will then break into smaller units and will leave the digestive tract after the bacteria degrade or erode the wooden spacers.

Figure 3:
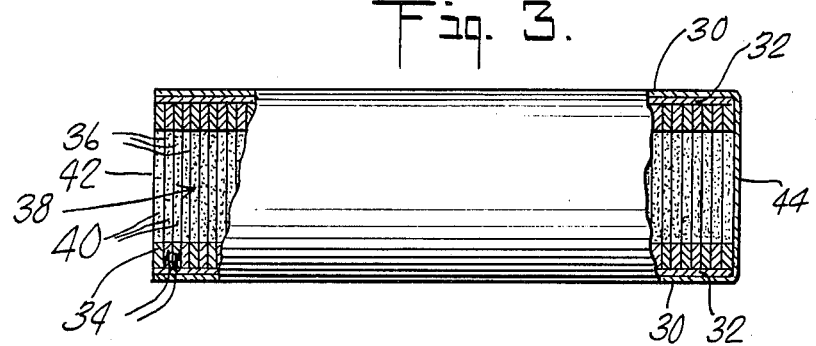
FIG. 3 is a view of another device adapted for the sustained release of therapeutic, additive or nutrient substances into the reticulorumen of a ruminant.

FIG. 3 illustrates a second embodiment of a bolus adapted to deliver therapeutic, additive or nutrient substances into the reticulorumen of a ruminant. The device shown in FIG. 3 is similar to the one shown in FIGS. 1 and 2 except that a metal shell 30, such as a stainless steel shell, serves as the weight means to impart the desired specific gravity to the bolus. Inside the metal shell is an epoxy coating 32, spacers 34, and partitions 36 which divide interior chamber 38 into compartments 40. In the embodiment shown, end 42 is open while end 44 is closed. Bacterial attack can come only from the direction of open end 42. Alternatively, both ends can be open and bacterial attack can come from both ends. The device works in a manner similar to that of the device illustrated in FIGS. 1 and 2.

In addition to feed additives, such as Rumensin ®, the device of the present invention may be used to dispense other substances, or combinations of substances, into the reticulorumen of a ruminant. These other substances include the following: rumen fermentation manipulators and ionophores, such as products sold under the trade names lasalocid, virginamycin, and ronnel, viable yeast cultures, sodium bicarbonate, mineral salts, zeolite, salinomyocin, and sarsoponin; minerals, especially in regions of acute mineral deficiency, such as phosphorus on the Gulf Coast, copper in Florida, magnesium in areas of grass tetany, and iodine in goiter areas; pharmaceuticals for the treatment of specific diseases, such as antibiotics and sulfa drugs; anthelmintics and other drugs, such as sedatives, antipyretics, hormones, and antibloating agents; fecal markers and "rumen-by-pass" materials.

The following example illustrates the use of the above described device.

Devices were constructed similar to the one illustrated in FIGS. 1 and 2. Each bolus was fabricated with partitions made of 75 lb. basis uncoated kraft paper. Each bolus was 100 mm long, 25 mm in diameter, and had 90 compartments. Each compartment was loaded with a dosage of Rumensin ® available from Elanco Products Co. Commercially available Rumensin ® is prepared by extending a concentrated form of the active ingredient with rice hulls. Commercially available Rumensin ® is so bulky that recommended levels of the active ingredient cannot be provided in a bolus of the size fabricated. In this example, each compartment contained a bulky (60 g./lb.) powdered Rumensin ® composition having 19.5 mg of active ingredient.

Twenty-four heifers averaging 625 lbs. were chosen for testing. The daily diet of each heifer comprised 6 lbs. of corn, 1.7 lbs. of a protein supplement, and orchard grass and white clover hay ad libitum. The heifers were kept on this diet for 86 days. A group of eight heifers, Group A, received two devices at the start of the test. Each bolus was dipped in mineral oil and administered orally to the heifers with a speculum. The heifers of Group A were thus scheduled to receive from the devices 39 mg of Rumensin ® per day. A second group of eight heifers, Group B, received 300 mg of Rumensin ® each in their daily supplement. The third group of eight heifers, Group C, was the control group and the heifers received no Rumensin ® in their diet.

Each animal's pen was searched daily to see if a bolus had been regurgitated or passed. Remnants of two devices were found in the pens of two animals on the 28th and the 38th days of the test respectively. Inspection of the remnants showed that some of the epoxy had eroded and that the devices had lost their integrity. Epoxies more resistant to erosion then the one employed are available commercially. The heifer that lost her devices on the 28th day was given two new ones on the 38th day.

The averaged results of the tests are presented in Table II.

TABLE II

|  | Group A (Bolus - No Rumensin ® in supplement) | Group A Heifers that retained their devices | Group B (No Bolus - Rumensin ® in supplement) | Group C (No Bolus - No Rumensin ® in supplement) |
| --- | --- | --- | --- | --- |
| Number of Heifers | 8 | 6 | 8 | 8 |
| Initial Weight (lbs.) | 630 | 598 | 623 | 621 |
| Daily Gain in Weight for 86 days (lbs./heifer/day) | 1.79 | 1.92 | 1.90 | 1.66 |
| Daily Gain in Weight for final 33 days of test (lbs./heifer/day) | 1.42 | 1.57 | 1.29 | 0.97 |
| Total Hay Consumption for 86 days (lbs.) | 822 | 837 | 593 | 789 |
| Feed Efficiency for 86 days (lbs. hay/lbs. gained) | 5.34 | 4.88 | 3.70 | 5.59 |

The daily gain in weight is measured more accurately than the feed efficiency and thus provides a better test for the utility of the device of the present invention. The data show that the heifers receiving Rumensin ® from the devices had a higher daily weight gain than the heifers which did not receive Rumensin ® (Group C). This was true during the entire test period and during the last 33 days of the test. The performance during the last 33 days shows that the devices were still functional at that time. The data also show that the six heifers that retained their devices throughout had a daily weight gain which was similar to or better than the heifers which received Rumensin ® in their supplement. Again, this was true for the entire length of the trial and for the last 33 days of the trial. The improved performance of the six heifers that retained their devices over the entire Group A heifers, including the two that lost their devices, also demonstrates the usefulness of the bolus. The increased daily weight gain experienced by heifers that received Rumensin ® either by bolus or by supplement is within the range observed by other workers.

Feed efficiency is calculated as the number of pounds of hay consumed per pound of weight gain. Thus, the lower the number, the more effective is the diet. The data for feed efficiency is not as significant as the data for daily weight gain. One reason is because calves have a tendency to throw hay out of their troughs. Nonetheless, the data for feed efficiency show that heifers receiving Rumensin ® through the bolus or from the supplement utilize their feed more effectively than heifers not receiving Rumensin ®.

It has previously been shown that Rumensin ® does not influence feed utilization unless given to animals in a controlled manner daily or at least on alternate days. See Muller, Potter, and Grueter, "Alternate Day vs. Daily Feeding of Supplements Containing Monensin to Pasture Cattle," Abstract from A.S.A.S. meeting at Cornell Univ., July 27-30, 1980. The results of the tests described herein show that a device according to the present invention releases Rumensin ® at the desired dosage rate.

In further research, it has been found that under certain diet conditions, such as 100% grass hay fed ad libitum, the bolus becomes clogged with hay particles after about 10 days. This slows the rate at which the partitions are degraded. Placing a nylon cloth across the open end will prevent this from occurring by allowing microbes to pass through but not hay particles.

While the invention has been described by reference to specific embodiments, this was for purposes of illustration only and should not be construed to limit the spirit and scope of the invention.

I claim:

1. A device for the prolonged administration of a substance into a fluid environment, comprising:
   a hollow body member having an interior chamber, and provided with an opening in fluid communication with the exterior of said body,
   said body made from a material which maintains its integrity during the administering period; and
   a plurality of serially arranged partitions positioned within said interior chamber
   said partitions made from a material which is degraded during the administering period upon exposure to the fluid environment exterior to said body,
   said partitions each releasing a dosage of the substance to be administered upon degradation of the partition,
   and arranged in an order to be contacted and degraded sequentially by fluid entering said opening thereby releasing sequentially the dosages of the substance into the first environment.

2. A device for the prolonged administration of a therapeutic, additive or nutrient substance into the reticulorumen of a ruminant, comprising:
   an elongated hollow body having an open end and a closed end, the open end of said body establishing fluid communication between the interior and the exterior of said body,
   said body made from a material which maintains its integrity in the reticulorumen environment;
   a plurality of partitions within said interior chamber and connected to or closely fitted against the interior walls of said body,
   said partitions made from a material which is degraded upon exposure to the reticulorumen environment,
   said partitions dividing said interior chamber into a series of compartments, each compartment containing a dosage of the substance to be administered,
   said partitions arranged in an order to be degraded sequentially upon exposure to the reticulorumen environment, thereby releasing sequentially the dosages of the substance into the reticulorumen; and
   retaining means at the closed end of said body to retain the device within the reticulorumen of the ruminant.

3. The device of claim 2 wherein the partitions are made from a cellulosic material.

4. The device of claim 3 wherein the cellulosic material is paper.

5. The device of claim 4 wherein the paper is 75 lb. basis uncoated kraft paper.

6. A device for the prolonged administration of therapeutic, additive or nutrient substance in the reticulorumen of a ruminant, comprising
   an elongated hollow body having an open end and a closed end, the open end of said body establishing fluid communication between the interior and exterior of said body,
   said body being made from a material which maintains its integrity in the reticulorumen environment,
   a plurality of partitions within said interior chamber and connected to or closely fitted against the interior walls of said body,
   said partitions being made from a material which is degraded upon exposure to the reticulorumen environment,
   said partitions dividing said interior chamber into a series of compartments, each compartment containing a dosage of a substance to be administered,
   spacers connected to or fitting closely against the interior walls of said body to keep the partitions apart,
   said partitions being arranged in an order to be degraded sequentially upon exposure to the reticulorumen environment, thereby releasing sequentially the dosages of the substance into the reticulorumen, and
   retaining means at the closed end of said body to retain the device within the reticulorumen of the ruminant.

7. The device of claim 6 wherein said spacers are made from a material which is degraded upon exposure to the reticulorumen environment.

8. The device of claim 7 wherein said spacers are made from a cellulosic material.

9. The device of claim 2 wherein said retaining means comprises weight means to impart to said device a specific gravity of at least about 1.5.

10. The device of claim 9 wherein said weight means comprises a metal ball.

11. The device of claim 9 wherein said weight means comprises a metal shell.

12. The device of claim 2 wherein said body is substantially cylindrical.

13. The device of claim 2 wherein said body is made from epoxy, polyethylene, or polypropylene.

14. The device of claim 13 wherein said body is made from epoxy.

15. The device of claim 2 wherein said body is made from metal or wood.

16. The device of claim 2 wherein said partitions are disposed transversely of said interior chamber and parallel to each other.

17. The device of claim 2 wherein said compartments contain a substance selected from the group consisting of feed additives, rumen fermentation manipulators, ionophores, minerals, drugs, and fecal markers.

18. The device of claim 1 wherein the partitions are made from paper.

19. The device of claim 18 wherein the paper is 75 lb. basis uncoated kraft paper.

20. A device for administering a biologically active substance into the digestive system of a ruminant comprising a body having a size and weight suitable for administration to and retention in the rumen of a ruminant, said body comprising a hollow interior and provided with an exterior surface substantially inert to the fluid contents of the rumen and having an opening to permit access of the fluid contents of the rumen to the interior of said body when said body is introduced into the rumen, the interior comprising a serial array or stack of partitions, said partitions making up said serial array or stack being biodegradable or disintegrable upon contact with the fluid contents of the rumen when said body is introduced into the rumen and said opening of said body being positioned so as to initially permit access of said fluid contents of the rumen to only the first or end partition or end partitions making up said array or stack within said body with the result that said partitions are serially or sequentially disintegrated as each of said partitions comes into contact with the fluid contents of said rumen, said partitions releasing material useful for the growth or well-being of the ruminant as each of said partitions disintegrates, and wherein said body is in the form of a cylinder having at least one open end, and wherein said partitions are made of cellulosic partitions disposed transversely within the interior of said body and connected to or closely fitting against the interior walls of said body, said partitions dividing said interior into a series of compartments, each compartment containing a dosage of the material useful for the growth or well-being of ruminant, and wherein spacers are provided connected to or fitting closely against the interior walls of said body to keep said partitions apart.

21. The device of claim 20 wherein said spacers are made from a material which is degraded upon exposure to the reticulorumen environment.

22. The device of claim 21 wherein said spacers are made from a cellulosic material.

23. The device of claim 20 wherein said device comprises weight means to impart to said device a specific gravity of at least about 1.5.

24. The device of claim 23 wherein said weight means comprises a steel ball.

25. The device of claim 23 wherein said weight means comprises a metal shell.

26. The device of claim 23 wherein said body is made from epoxy.

27. The device of claim 26 wherein said partitions are parallel to each other.

28. The device of claim 27 wherein said compartments contain a substance selected from the group consisting of feed additives, rumen fermentation manipulators, ionophores, minerals, drugs, and fecal markers.

29. The device of claim 28 wherein said body is in the form of a cylinder having at least one open end and is provided with a plurality of cellulosic partitions disposed transversely within said interior chamber and connected to or closely fitting against the interior walls of said body, said partitions dividing said interior chamber into a series of compartments, each compartment containing a dosage of the substance to be administered, whereby upon disintegration of said partitions the dosages of the substance are released sequentially into the reticulorumen of the ruminant.

30. The method of claim 29 wherein the therapeutic, additive or nutrient substance is selected from the group consisting of feed additives, rumen fermentation manipulators, ionophores, minerals, drugs, and fecal markers.

31. A device for administering a biologically active substance into the digestive system of a ruminant comprising:

a body having a size and weight suitable for administration to and retention in the rumen of a ruminant, said body comprising a hollow interior and provided with an exterior surface substantially inert to the fluid contents of the rumen and an opening to permit access of the fluid contents of the rumen to the interior of said body when said body is introduced into the rumen, the interior of said body comprising a serial array or stack of partitions, said partitions making up said serial array or stack being biodegradable or disintegrable upon contact with the fluid contents of the rumen into which said body is introduced and said opening of said body being positioned so as to initially permit access of said fluid contents of the rumen to only the first or end partition or end partitions making up said array or stack within said body with the result that said partitions are serially or sequentially disintegrated as each of said partitions comes into contact with the fluid contents of said rumen, said partitions releasing material useful for the growth or well-being of the ruminant as each of said partitions disintegrates.

32. A method for the prolonged administration of a therapeutic, additive or nutrient substance into the reticulorumen of a ruminant, comprising:

incorporating an effective amount of the therapeutic, additive or nutrient substance into the device of claim 1, 2, or 26, and introducing said device into the reticulorumen of a ruminant.

33. The method of administering to a ruminant a biologically active substance in a sequence of dosages over an extended period of time which comprises introducing into the reticulorumen of a ruminant a device as defined in claim 31.

34. The method of treating a ruminant which comprises administering orally to a ruminant a device as defined in claim 32.

35. The method of treating a ruminant which comprises introducing into the reticulorumen of the ruminant a device which sequentially dispenses a biologically active substance into the digestive tract of the ruminant over an extended period of time, said device having a sufficiently high specific gravity within the range of 1.5 to 7 to remain in the reticulorumen and comprising a plurality of doses of said substance separated from the fluid environment of the reticulorumen and from one another by a plurality of biodegradable barriers which are sequentially biodegraded in the reticulorumen environment thereby releasing the biologically active material into the digestive tract of the animal in successive dosages over an extended period of time as said barriers are successively degraded by exposure to the reticulorumen environment.

36. The method of dispensing a substance into a fluid environment in sequential dosages over an extended period of time which comprises introducing into said fluid environment a physically and chemically stable hollow tubular member open at one end and substantially closed at the other and comprising a plurality of doses of said substances separated by a stacked array of partitions within the interior of said tubular member, said partitions comprising a material which is degraded upon exposure to the fluid environment arranged in an order to be degraded sequentially upon exposure to the fluid environment thereby releasing sequentially the dosages of the substance into the said environment.

37. The method of claim 36 wherein the environment is the reticulorumen of a ruminant and the partitions are paper.

38. A device for the prolonged administration of a biologically active substance into the body of a live animal which comprises:

a non-biodegradable hollow cylindrical body member open at one end, a plurality of biodegradable partitions positioned within said body member dividing the interior thereof into a series of compartments, and a dosage of said biologically active substance in each compartment, said partitions arranged in an order to be degraded sequentially in the biological environment within the body thereby releasing sequentially the dosages of said biologically active substance into the live animal.

39. A device for the administration of a biologically active substance to a ruminant over an extended period of time which comprises, a non-biodegradable elongated hollow body member open at one end and weighted at the other, a plurality of biodegradable barriers within said body forming a plurality of closed compartments each containing a dosage of a substance to be administered to the ruminant by introduction into the reticulorumen of the ruminant, said barriers arranged in an order to disintegrate sequentially upon exposure to the reticulorumen environment thereby releasing sequentially the doses of the substance into the digestive tract of the ruminant.

* * * * *